(12) United States Patent
Clifford

(10) Patent No.: US 6,203,514 B1
(45) Date of Patent: Mar. 20, 2001

(54) TAMPON CONTAINING A MEDICINAL LIQUID IMPARTED FROM A TAMPON IRRIGATION SYRINGE

(76) Inventor: Charles K. Clifford, 1409 Brentwood Pl., Sanford, NC (US) 27330

( * ) Notice: Subject to any disclaimer, the term of this patent is extended or adjusted under 35 U.S.C. 154(b) by 0 days.

(21) Appl. No.: 09/252,765

(22) Filed: Feb. 19, 1999

(51) Int. Cl.[7] ........................................ A61F 13/20
(52) U.S. Cl. ............................................ 604/11; 604/904
(58) Field of Search .................... 604/11–15, 285–288, 604/905, 358, 367, 368

(56) References Cited

U.S. PATENT DOCUMENTS

| 2,340,311 | * | 2/1944 | Donovan . |
| 3,902,493 | | 9/1975 | Baier et al. . |
| 4,200,101 | * | 4/1980 | Glassman . |
| 4,215,692 | * | 8/1980 | Levesque . |
| 4,270,977 | | 6/1981 | Herman et al. . |
| 4,274,410 | | 6/1981 | Chvapil . |
| 4,286,596 | | 9/1981 | Rubinstein . |
| 4,305,391 | * | 12/1981 | Jackson . |
| 4,309,997 | * | 1/1982 | Donald . |
| 4,318,404 | * | 3/1982 | Cunningham . |
| 5,163,583 | | 11/1992 | Whitworth . |
| 5,201,326 | | 4/1993 | Kubicki et al. . |
| 5,286,453 | | 2/1994 | Pope . |
| 5,344,666 | | 9/1994 | Levine . |
| 5,417,224 | * | 5/1995 | Petrus et al. . |

FOREIGN PATENT DOCUMENTS 0 437 816 A1   7/1991   (EP) .

* cited by examiner

Primary Examiner—John G. Weiss
Assistant Examiner—David J. Cho
(74) Attorney, Agent, or Firm—Jenkins & Wilson, P.A.

(57) ABSTRACT

A tampon device including a medicinal liquid, such as a hemostatic agent solution, and useful for releasing the medicinal liquid into the vaginal cavity after insertion into the vaginal cavity.

4 Claims, 3 Drawing Sheets

TAMPON CONTAINING A MEDICINAL LIQUID IMPARTED FROM A TAMPON IRRIGATION SYRINGE

TECHNICAL FIELD

The present invention relates, in general, to tampons. More particularly, the present invention relates to a tampon that contains a medicinal liquid, such as a hemostatic agent solution, which is useful, for instance, for insertion into the vaginal canal after cervical surgery, such as surgery to remove a conical section of the cervix with a scalpel to test the section for cancer because of a previous positive PAP smear.

BACKGROUND OF THE INVENTION

Tampons are well known in the art. Nowadays, tampons typically have excellent absorbency as they are usually made from a combination of superabsorbent polymer particles and fluff (i.e. fibrous material such as cellulosic fiber, cotton fiber, linen fiber, polymeric fiber, or a combination thereof) by well known processes. Methods for blending the superabsorbent polymer particles and the fluff, such as the wet-laid process or the air-laid process, to make a composite useful in the manufacture of tampons are well known, and are discussed in European Published Patent Application No. 0 437 816 A1 to Kim and Nielsen, assignors to Hoechest Celanese Corporation, and U.S. Pat. No. 4,270,977 to Herman and Kruse. Of course, tampons do not have to be extremely absorbent, and thus can be manufactured of fluff, absent any superabsorbent polymer particles.

Additionally, it is known to include some kind of medicament with a tampon for delivery of the medicament after the tampon is inserted into the vaginal canal. Such tampons are described in U.S. Pat. No. 5,201,326 to Kubicki and Rink, assignors to VP-Schickedanz, which shows a fibrous tampon body surrounded by a hardened collagen foam, where the foam is impregnated with the medicament to be released. Moreover, U.S. Pat. No. 4,286,596 to Morton Rubinstein, assignor to Herbert Rubinstein, shows a tampon body, having disposed within it, a rupturable container holding a liquid medicament, and U.S. Pat. No. 3,902,493 to Baier and Trokhan, assignors to The Proctor & Gamble Company, shows a tampon body, having disposed about it, a medicament-containing hydrophobic overwrap.

Also, of background interest is U.S. Pat. No. 4,274,410 to Chvapil, assignor to Medi-Coll, Inc. which shows an annular contraceptive device that is made for insertion in the vaginal canal proximate the cervix and that is made from collagen and cellulosic fiber, where the collagen is impregnated with a spermicide.

The disclosures of all patents and published patent applications mentioned in this specification are incorporated by reference.

Nevertheless, it is still desirable to have a simpler tampon containing a liquid medicament, such as a hemostatic agent solution, for release of the liquid into the vaginal canal.

SUMMARY AND OBJECT OF THE INVENTION

Accordingly, the present invention provides for a tampon comprising a fibrous portion including a medicinal liquid, wherein the fibrous portion is impregnated with a medicinal liquid such as a hemostatic agent solution.

Additionally, the present invention provides for a method of making a tampon including a medicinal liquid. The method comprises: (a) providing a tampon having a fibrous portion; (b) inserting a dispenser, such as a syringe, having a barrel portion and a hollow needle portion and containing a medicinal liquid, with the needle portion into the fibrous portion; (c) dispensing the medicinal liquid from the dispenser into the fibrous portion; and (d) removing the dispenser.

Hence, it is an object of the present invention to obviate the prior art problem of having a separate and additional structural element of the tampon, such as the hardened collagen cover surrounding the tampon body described in the above-noted U.S. Pat. No. 5,201,326, or the rupturable container disposed inside the tampon body described in the above-noted U.S. Pat. No. 4,286,596 to Rubinstein, for including a medicament.

Therefore, it is an advantage of the present invention that the method of making the tampon containing a medicinal liquid is simple and that the resultant tampon containing a medicinal liquid is free of additional structural elements as compared to prior art tampons that include a medicament.

Consequently, it is a feature of the present invention that the tampon containing a medicinal liquid, such as a hemostatic agent solution, can be made by impregnating the tampon body of a standard tampon of the art with a medicinal liquid.

Some of the objects of the invention having been stated above, other objects will become evident as the description proceeds, when taken in connection with the accompanying drawings as best described below.

DETAILED DESCRIPTION OF THE INVENTION

In the present invention, the tampon has a fibrous body portion. The fibrous portion includes a medicinal liquid, such as a hemostatic agent solution.

During manufacture of the tampon, the medicinal liquid may be intermixed with the fluff, i.e., the fiber, in order to impregnate the fiber with the medicinal liquid. Optionally, superabsorbent polymer particles may also be admixed with the fluff and the medicinal liquid. However, it is preferred not to have present such superabsorbent polymer particles because, since they are excellent for absorbing catamenial discharge during mensus, they also will tend to retain the medicinal liquid and interfere with its being released from the tampon into the vaginal canal.

In an alternative embodiment, already made tampons, which may be standard prior art tampons (which of course do not include any medicinal liquid) can be employed for making the inventive tampon containing a medicinal liquid.

Figure 1:
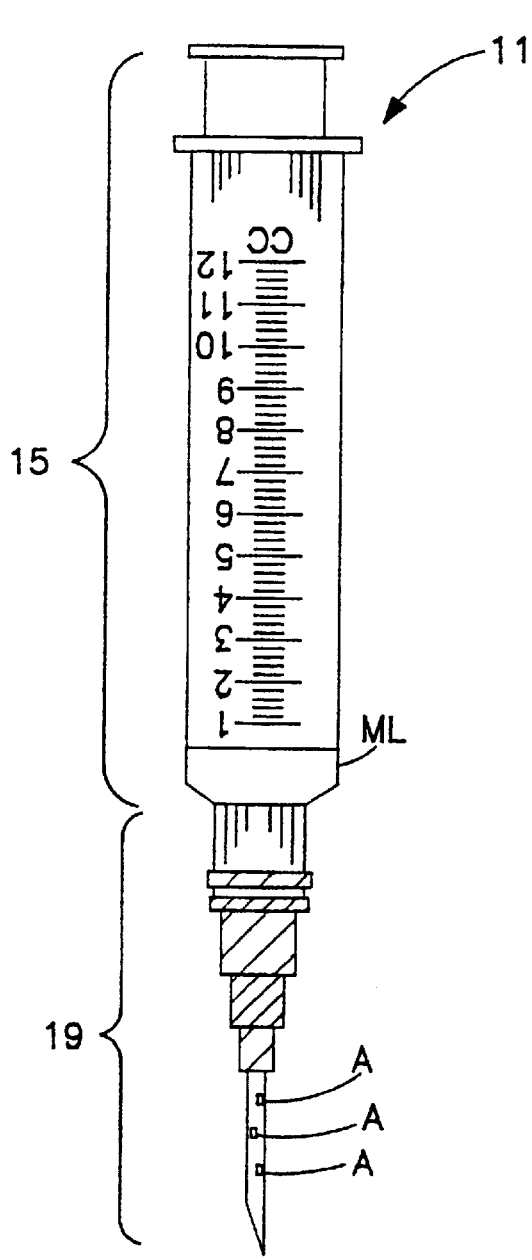
FIG. 1 depicts a preferred embodiment of a dispenser, showing a syringe with a barrel and hollow needle combination useful for impregnating a tampon with a medicinal liquid.

In this embodiment, a dispenser having a combination barrel and hollow needle, such as a hypodermic syringe, depicted as tampon irrigation syringe 11, having in combination a piston portion or a barrel portion 15 and a hollow needle portion 19, which is illustrated in FIG. 1, may be employed for impregnating a tampon body portion of an already existing tampon 21 (see FIG. 5) with a medicinal liquid ML.

Figure 3:
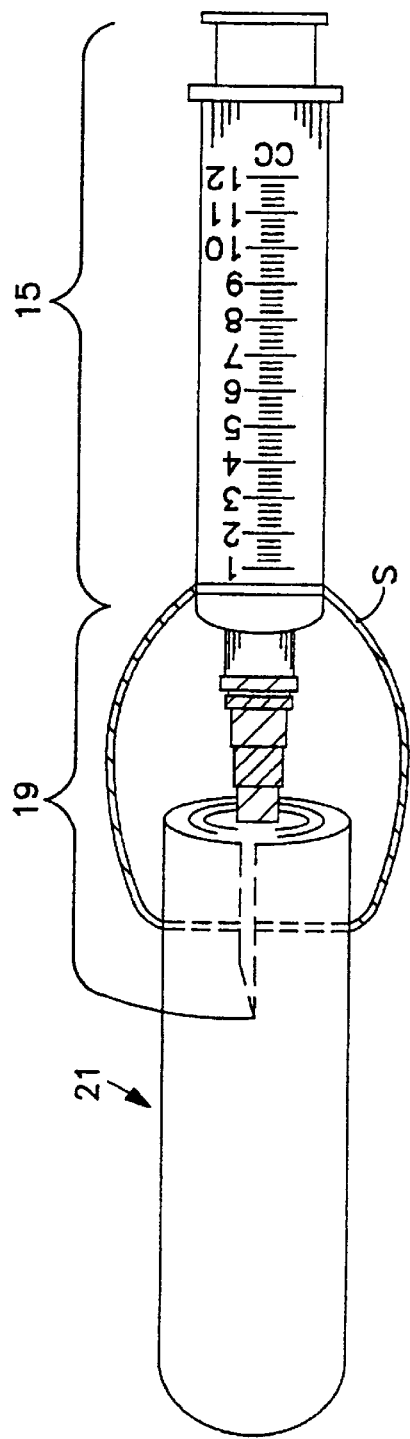
FIG. 3 depicts a tampon having inserted in it the hollow needle portion of the dispenser of FIG. 1.
Figure 4:
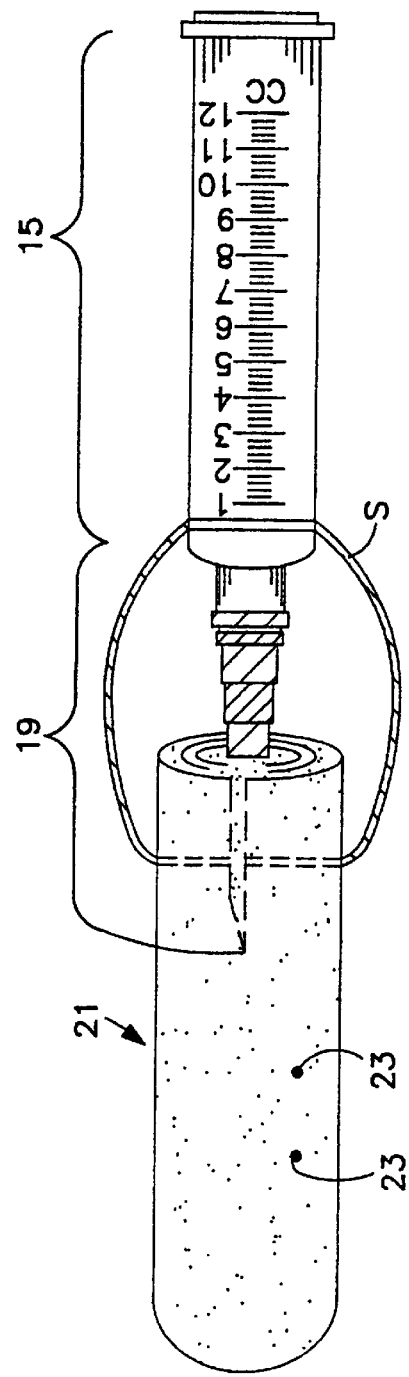
FIG. 4 is like FIG. 3, but with the plunger of the barrel portion of the dispenser down so that the tampon is now impregnated with medicinal liquid.

Employed for impregnating the tampon body may be any known in the art hypodermic syringe, depicted here as tampon irrigation syringe 11, having a small piston or barrel portion 15 and having a detachable, hollow needle 19 with standard opening at the end thereof, which is generally used for injecting solutions subcutaneously. As can be seen from FIGS. 3 and 4, barrel portion 15 is filled with a selected amount of medicinal liquid ML and attached to needle portion 19, followed by needle portion 19 being inserted into tampon 21, and then the plunger of piston or barrel portion 15 is pushed down in order to dispense the medicinal liquid ML into tampon 21 and impregnate the fiber thereof. Tampon irrigation syringe 11 is then removed.

Figure 2:
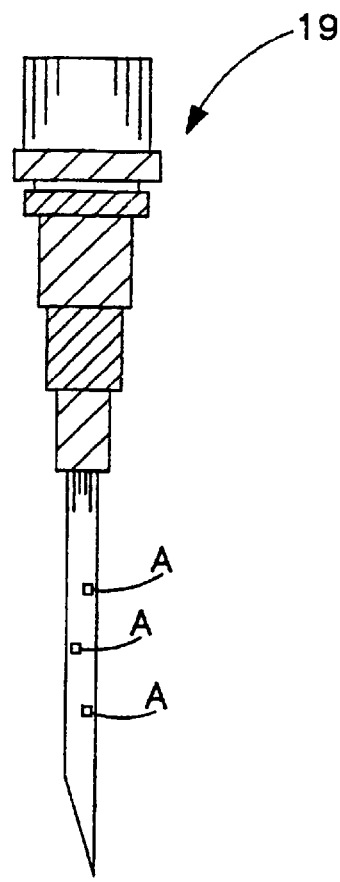
FIG. 2 is an enlargement of the hollow needle portion of the combination of FIG. 1 in order to illustrate more clearly a preferred embodiment of the needle portion having multiple apertures.

FIG. 2 shows an enlarged view of needle portion 19 of FIG. 1. In order to help disperse medicinal liquid ML throughout the longitudinal length of a tampon 21, it is preferred to employ tampon irrigation syringe 11 having hollow needle portion 19 where the needle portion, in addition to the standard opening at the end thereof, contains a multiplicity of apertures A along its shaft, as is illustrated in FIG. 2.

Figure 5:
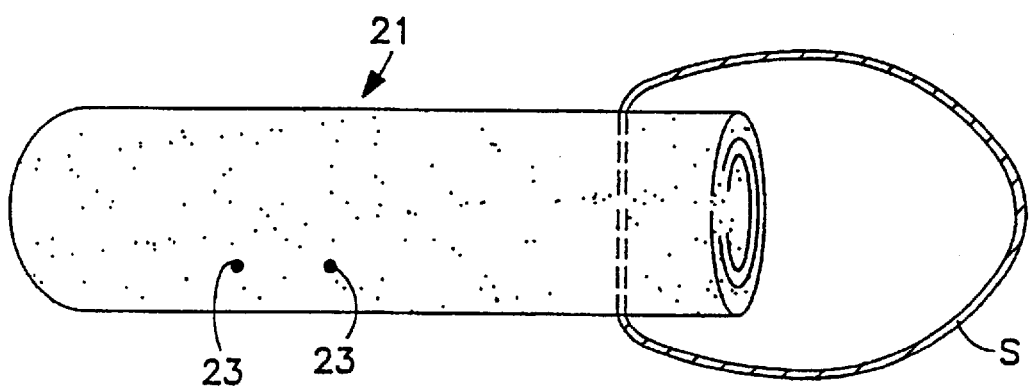
FIG. 5 depicts a tampon made of fibrous material and impregnated with medicinal liquid.

In FIG. 5, illustrated is a tampon 21 made of fibrous material and having string S (for removal of the tampon from the vaginal canal) and including areas 23 of impregnated medicinal liquid ML.

In addition to hypodermic syringes, various dispenser devices having a barrel and hollow needle, such as those disclosed in U.S. Pat. No. 5,286,453 to Pope and U.S. Pat. No. 5,344,666 to Levine, may be employed for impregnating the fibrous portion of a tampon with a medicinal liquid.

During use, the tampon containing the medicinal liquid is inserted into the vaginal canal, so that the medicinal liquid may release from the tampon and into the vaginal canal.

Various medicinal liquids may be employed in addition to a hemostatic agent solution. For instance, the medicinal liquid may be a solution of an anti-bacterial agent, an anti-viral agent, or an anti-yeast agent, and then the impregnated tampon may be used for treating various vaginal infections.

In the preferred embodiment, use is after cervical surgery that was done to remove a portion of the cervix after a previous positive PAP smear. Bleeding is a common complication of such surgery, and thus, in this instance, the medicinal liquid would be a solution containing a hemostatic agent, such as ferric subsulfate (also known as Monsel's solution).

It will be understood that various details of the invention may be changed without departing from the scope of the invention. Furthermore, the foregoing description is for the purpose of illustration only, and not for the purpose of limitation—the invention being defined by the claims.

What is claimed is:

1. A combination tampon and dispenser comprising (a) a tampon that has a fibrous portion including a medicinal liquid, wherein the medicinal liquid is impregnated in the fibrous portion and wherein the impregnated tampon is free of additional structural elements for including the medicinal liquid, and (b) a dispenser that has a barrel portion and a hollow needle portion, where the hollow needle portion contains a multiplicity of apertures along its shaft.

2. The tampon of claim 1, wherein the medicinal liquid is a solution selected from the group consisting of a hemostatic agent solution, an anti-bacterial agent solution, an anti-viral agent solution, or an anti-yeast solution.

3. The tampon of claim 1, wherein the fibrous portion is made of fibers selected from the group consisting of cellulosic fibers, cotton fibers, linen fibers, polymeric fibers, and combinations thereof.

4. The tampon of claim 1, further including superabsorbent polymer particles admixed with the fibrous portion.

* * * * *